US00PP08570P

United States Patent [19]

Marshall

[11] Patent Number: Plant 8,570

[45] Date of Patent: Feb. 1, 1994

[54] "MARSHALL ROSE" NECTARINE TREE

[76] Inventor: Richard J. Marshall, 6321 Avenue 376, Dinuba, Calif. 93618

[21] Appl. No.: 979,074

[22] Filed: Nov. 19, 1992

[51] Int. Cl.[5] ..... A01H 5/00
[52] U.S. Cl. ..... Plt./40.1
[58] Field of Search ..... Plt. 40.1

*Primary Examiner*—James R. Feyrer
*Assistant Examiner*—Bruce R. Campell
*Attorney, Agent, or Firm*—Worrel & Worrel

[57] ABSTRACT

A new and distinct variety of nectarine tree producing fruit which are mature for harvesting and shipment approximately June 9 to July 2 in the San Joaquin Valley of central California with skin which has a dark red coloration at harvest with distinctive white flesh and the fruit being cling to semi-freestone by nature.

1 Drawing Sheet

BACKGROUND OF THE NEW VARIETY

The present invention relates to a new and distinct variety of nectarine tree which will hereinafter be denominated varietally as the "Marshall Rose" nectarine tree and, more particularly, to a nectarine tree which produces fruit which are mature for harvest approximately June 9 through July 2 in the San Joaquin Valley of central California, the fruit being a cling to semi-freestone and which has a distinctive white flesh with a dark red skin coloration.

New varieties of fruit trees can be distinguished by a host of different characteristics. These distinguishing characteristics can include one or more rather typical identifiers such as ripening date, skin coloration, flesh coloration, size, shape, flavor and stone attachment. They can also include more obscure identifiers such as the marginal form of the leaves, the number of stem glands, the number of stamens in the flower and the like. Obviously, some of these characteristics are of no commercial significance.

In some instances the principal distinguishing characteristics of a new variety include two or more characteristics which are particularly unusual in their combination. Where this combination is of commercial significance, the new variety may be of substantial commercial value. The new variety of the present invention is particularly attractive in these regards in that it has a distinctive white flesh, contrasting dark red skin color and an early ripening date for a white fleshed nectarine.

ORIGIN AND ASEXUAL REPRODUCTION OF THE NEW VARIETY

The present variety of nectarine tree was discovered by the inventor in 1987 in an orchard at a dairy ranch then under his direction which is located in Kingsburg in the San Joaquin Valley of central California. The applicant discovered the new variety as a sport of the "Snowflame" peach tree (U.S. Plant Pat. No. 5,251). In 1988, the inventor asexually reproduced the new variety by grafting four onto mature orchard peach trees of the "Snowflame" variety located at 38030 Brewer Drive, Kingsburg, Calif. In succeeding years the inventor has observed the asexually reproduced trees of the new variety and confirmed that they possess precisely the same characteristics as those of the original sport of the new variety.

SUMMARY OF THE NEW VARIETY

The "Marshall Rose" nectarine tree is characterized principally as to novelty by producing early ripening, white fleshed, cling to semi-freestone fruit which are mature for commercial harvesting and shipment approximately June 9 to July 2 in the San Joaquin Valley of central California; which have a distinctive dark red skin coloration; and which possess an appealing flavor well suited to the commercial market.

BRIEF DESCRIPTION OF THE DRAWING

The accompanying drawing is a color photograph showing fruit of the new variety including one in bottom plan view showing the stem thereof;

a second in side elevation showing the suture;

a third in top plan view showing the apex; and a fourth sectioned in a plane at right angles to the longitudinal axis of the fruit and showing the stone in place with fibers remaining attached thereto; a stone from fruit of the new variety; and typical foliage of the new variety.

DETAILED DESCRIPTION

Referring more specifically to the pomological details of this new and distinct variety of nectarine tree, the following has been observed under the ecological conditions prevailing in Kingsburg, Calif. All major color code designations are by reference to the *Dictionary Of Color*, Second Edition, 1950, A. Maerz and M. Rea Paul, McGraw-Hill Book Co., Inc., New York, N.Y.

TREE

Generally:

*Size.*—Medium.

*Productivity.*—Productive.

*Figure.*—Spreading.

*Regularity of bearing.*—Regular.

Trunk:

*Diameter in relation to length.*—Stocky.

*Surface texture.*—Medium.

Branches:

*Size.*—Medium.

*Surface texture.*—Medium.

*Color.*—Page 37, Plate 7, C-7, Bonito Fuscoust.

*Lenticels — numbers.*—Numerous.

*Lenticels — size.*—1.5 mm (0.059 inches) to 2 mm (0.078 inches) by 4 mm (0.157 inches) to 9 mm (0.354 inches).

LEAVES

Size:
*Generally.*—Large.
*Average length.*—190 mm (7.480 inches) to 200 mm (7.874 inches).
*Average width.*—45 mm (1.771 inches) to 48 mm (1.889 inches).

Form:
*Shape.*—Lanceolate.

Color:
*Upwardly disposed surface.*—Page 71, Plate 24. J-12, Chrome Gr, Deep.
*Downwardly disposed surface.*—Page 67, Medium Green, Plate 22, B-8.

Marginal form: Finely serrate.

Glandular characteristics: 1, Reniform. Green with reddish center.

Petiole:
*Length.*—9 mm (0.354 inches) to 12 mm (0.472 inches).
*Thickness.*—2 mm (0.078 inches).

Stem glands:
*Number.*—Two.
*Position.*—Opposite each other.
*Size.*—Small.
*Color.*—Green.
*Type.*—Reniform.

Stipules: None.

FLOWERS

Flower buds:
*Shape.*—Simple bud.
*Size.*—Width — 8 mm (0.3149 inches). Length — 11 mm (0.4330 inches).
*Surface.*—Glaucous.

Date of first bloom: Feb. 24, 1992 in San Joaquin Valley of central California.

Date of full bloom: Mar. 6, 1992.

Petal drop: Mar. 13, 1992.

Size:
*Generally.*—First sample: 40 mm (1.574 inches) by 46 mm (1.811 inches). Second sample: 43 mm (1.692 inches) by 47 mm (1.850 inches).

Petals:
*Color.*—Page 123, Plate 50, D-3, Cameo Pk.

Nectaries: None.

Stamens: Thirty-nine to forty-six.

Pistil: One.

FRUIT

Maturity when described: Ripe for commercial harvesting and shipment approximately Jun. 9, 1992 to Jul. 2, 1992 at Kingsburg in the San Joaquin Valley of central California. The yellow-fleshed nectarine tree, "Tasty Gold" matures about three or four days later than the "Marshall Rose" nectarine tree in the Kingsburg area. The white-fleshed nectarine, "Artic Rose" matures no sooner than June 20 in the same area.

Size:
*Average diameter in the suture plane.*—62 mm (2.440 inches) to 65 mm (2.559 inches).
*Average diameter transverse to suture plane.*—62 mm (2.440 inches) to 68 mm (2.677 inches).
*Average diameter transverse and at right angles to the suture plane.*—60 mm (2.362 inches) to 63 mm (2.480 inches).

Form:
*Uniformity.*—Uniform.
*Symmetry.*—Symmetrical-Globose.

Suture:
*Generally.*—Inconspicuous line, slightly depressed, with marked depression beyond pistil point.
*Length.*—90 mm (3.543 inches) to 105 mm (4.133 inches).

Ventral surface:
*Generally.*—Round at base, slightly lipped near pistil point.

Stem cavity:
*Generally.*—Obtuse.
*Length.*—22 mm (0.866 inches).
*Width.*—17 mm (0.669 inches).
*Depth.*—8 mm (0.314 inches).

Base: Rounded.

Apex: Rounded.

Stem:
*Length.*—8 mm (0.314 inches).
*Width.*—3 mm (0.118 inches).

Pistil point: Depressed.

Both the "Tasty Gold" and "Artic Rose" nectarine trees are smaller in size as compared to the "Marshall Rose" nectarine tree.

Skin:
*Thickness.*—Medium.
*Texture.*—Medium.
*Tendency to crack.*—None.
*Color.*—Ground color — Page 41, Plate 9, B-1; Blush color — Page 35, Plate 6, K-5 Clove, Pk.
*Pubescence.*—None.

Flesh:
*Flesh color.*—Page 41, Plate 9, A-1.
*Surface of pit cavity.*—Rough.
*Color of pit well.*—Same as flesh.
*Flavor.*—Subacid.
*Aroma.*—Wanting.
*Texture.*—Medium, melting.
*Juice.*—Juicy.
*Fibers — numbers.*—Few.
*Amygdalin.*—Scant.
*Ripening.*—Even.
*Eating quality.*—Good.

Stone:
*Attachment.*—Cling to semi-freestone.
*Fibers.*—Several — Fine.
*Size — length.*—32 mm (1.259 inches) to 35 mm (1.377 inches).
*Size — width.*—24 mm (0.944 inches) to 26 mm (1.023 inches).
*Size — thickness.*—20 mm (0.787 inches) to 21 mm (0.826 inches).
*Form — generally.*—Oblong, obovate.
*Color.*—Page 43, Plate 10, C-4, Sunset.
*Sides.*—Equal, pitted near base, ridged near apex.
*Ridges.*—Rounded.
*Base.*—Straight.
*Size and position of grooves.*—Deep near apex.
*Dorsal edge.*—Narrow with shallow groove throughout.
*Ventral edge.*—Thin with wing throughout.
*Splitting tendency.*—None.

Use: Fresh market.

Keeping quality: Good.

Shipping and handling qualities: Good.

Resistance to disease: Good.

Although the new variety of nectarine tree possesses the described characteristics noted above as a result of the growing conditions prevailing near Kingsburg, Calif. in the San Joaquin Valley of central California, it is to be understood that variations of the usual magnitude and characteristics incident to changes in growing conditions, fertilization, pruning, irrigation, pest control and the like are to be expected.

Having thus described and illustrated my new variety of nectarine tree, what I claim as new and desire to be secured by Plant Letters Patent is:

1. A new and distinct variety of nectarine tree substantially as illustrated and described characterized by producing cling to semi-freestone fruit which are mature for commercial harvesting and shipment approximately June 9 to July 2 in the San Joaquin Valley of central California, which have a distinctive white flesh, a dark red skin coloration and a pleasing flavor.

* * * * *

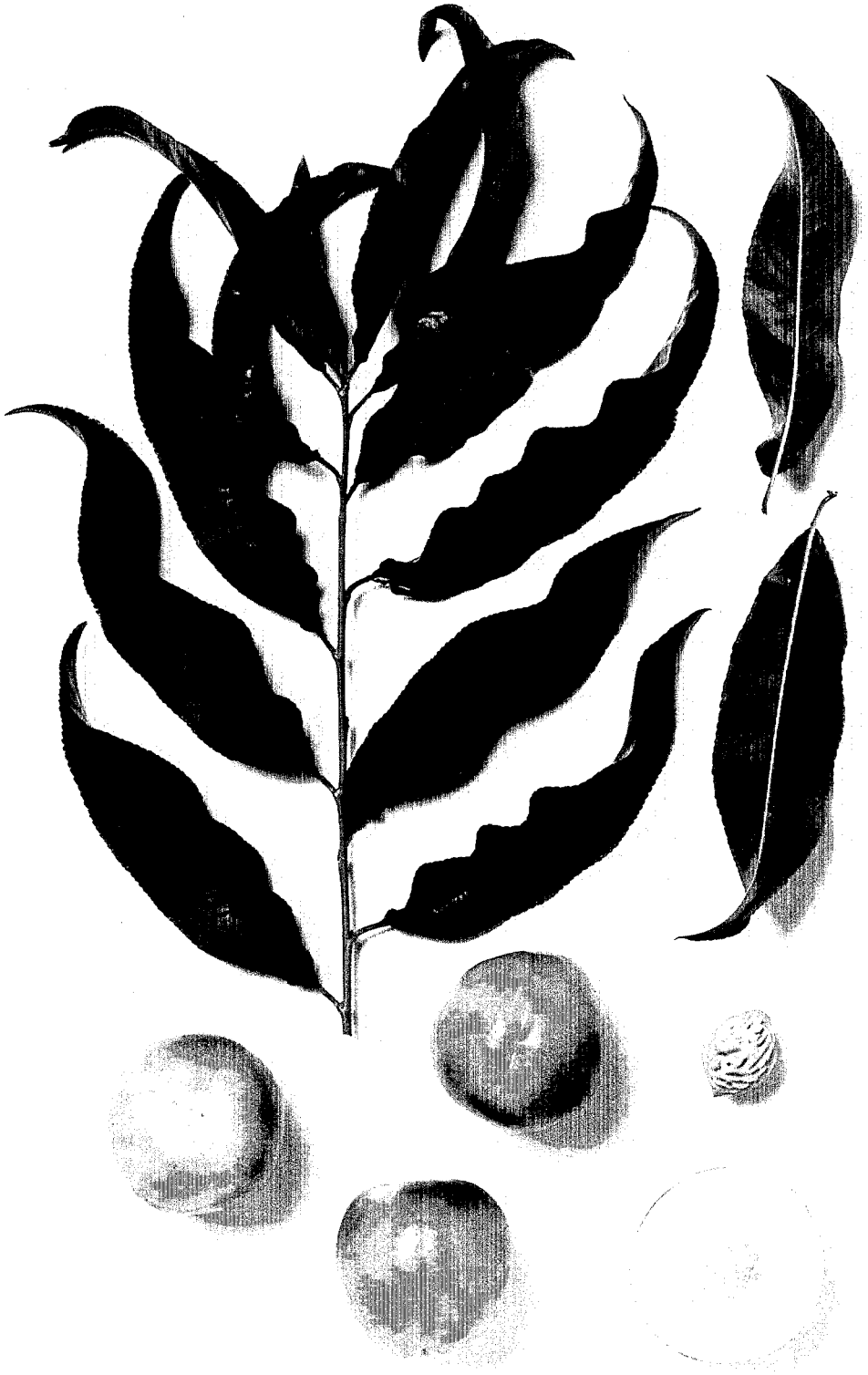

UNITED STATES PATENT AND TRADEMARK OFFICE

CERTIFICATE OF CORRECTION

PATENT NO. : PP 8,570

DATED : February 1, 1994

INVENTOR(S) : Richard J. Marshall

It is certified that error appears in the above-indentified patent and that said Letters Patent is hereby corrected as shown below:

Column 1, line 43, delete "four onto" and substitute --onto four--.

Signed and Sealed this

Fourth Day of October, 1994

*Attest:*

Bruce Lehman

BRUCE LEHMAN

*Attesting Officer*

*Commissioner of Patents and Trademarks*